United States Patent [19]

Naylor

[11] Patent Number: 4,466,978
[45] Date of Patent: Aug. 21, 1984

[54] BODYWEIGHT REDUCING METHOD

[75] Inventor: Graham J. Naylor, Lulgate, Lucklawhill Balmullo, St. Andrews, KY16 OBQ, Fife, Scotland

[73] Assignees: Graham John Naylor; Pamela Hilda Naylor, both of St. Andrews, Scotland

[21] Appl. No.: 354,016

[22] Filed: Mar. 2, 1982

[30] Foreign Application Priority Data

Dec. 10, 1981 [GB] United Kingdom ............... 8137294

[51] Int. Cl.$^3$ ............... A61K 31/365; A61K 31/54; A61K 31/16
[52] U.S. Cl. ................... 424/280; 424/247; 424/320
[58] Field of Search ............... 424/247, 280

[56] References Cited
FOREIGN PATENT DOCUMENTS
46-9358 9/1971 Japan ............... 424/280

OTHER PUBLICATIONS
Handbook of Nonprescription Drugs, 5th ed., Am. Pharm. Assoc., pp. 177-183, (1977).
Chem. Abst. 92, 40252(q), (1980), Odumosu et al.

*Primary Examiner*—Douglas W. Robinson
*Attorney, Agent, or Firm*—Murray, Whisenhunt and Ferguson

[57] ABSTRACT

The present invention provides in one aspect a slimming method and in a further aspect a method for the treatment or prophylaxis of obesity, comprising the administration of a bodyweight reducing effective dosage of a compound selected from glutathione, physiologically acceptable salts and esters thereof, and ascorbic acid, and physiologically acceptable salts and esters thereof, and a compound of Formula I

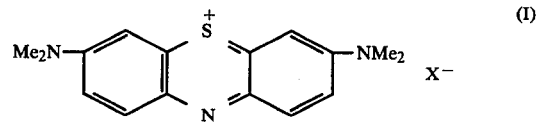

(I)

wherein X is a physiologically acceptable anion, and bioprecursors thereof, to a subject.

6 Claims, No Drawings

BODYWEIGHT REDUCING METHOD

This invention relates to a method of reducing bodyweight.

There has for many years been a considerable demand for safe and effective methods of slimming and treating obesity in order to improve the aesthetic appearance of the person's body and make that person appear more physically attractive to others at one end of the spectrum and to reduce clinical obesity at the other end. On the one hand though many relatively safe methods such as exercise and carefully controlled diets have limited effectiveness due to the fact that many people find these methods difficult to adhere to over an extended period of time. Other methods on the other hand can have deleterious effects on the human metabolism.

It is an object of the present invention to avoid or minimize one or more of the above disadvantages and in particular to provide a new slimming method and a method for the treatment or prophylaxis of obesity.

The present invention provides in one aspect a slimming method and in a further aspect a method for the treatment or prophylaxis of obesity, comprising the administration of a body-weight reducing effective dosage of a compound selected from glutathione, physiologically acceptable salts and esters thereof, and ascorbic acid, and physiologically acceptable salts and esters thereof, and a compound of Formula I

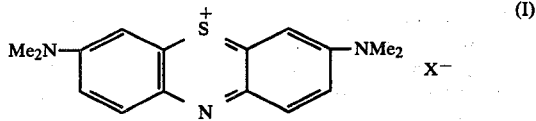

wherein X is a physiologically acceptable anion, and bioprecursors thereof, to a subject.

Preferably there is used a compound of Formula I in which the anion is a halide anion especially chloride. In the latter case the compound of formula I is known as methylene blue or 3,7-bisdimethylaminophenothiazine hydrochloride having the chemical formula $C_{16}H_{18}ClN_3S$. Other suitable anions which may be mentioned include sulphate, nitrate, citrate, carbonate and fumarate.

For the avoidance of doubt the substance referred to hereinabove as glutathione is the compound having the name:

γ-L-glutamyl-L-cysteinylglycine (oxidised or reduced form) and the chemical formula $HO_2CCH(NH_2)CH_2CH_2CONHCH(CH_2SH)CONHCH_2CO_2H$ (in the case of the reduced form).

As well as being substantially free from the above-mentioned disadvantages of prior art methods to a greater or lesser extent, the present invention has additional advantages in that the above compounds are relatively inexpensive and readily available.

As indicated above the present invention extends to the administration of a bioprecursor of a compound specified above, namely a compound which is readily converted in the human body upon administration into a said compound of the invention.

The compounds of the method of the invention are well known from the literature as also are their methods of preparation and/or extraction. Particular desired salts or precursors can be readily produced by standard procedures such as metathetical reactions.

The inventor has found that the compounds of the invention have significant in vitro and in vivo activity in the reversal and/or catalysis of reversal, of Na-K ATPase inhibition caused in the body by, in particular, vanadate ions. It is believed that this is achieved by the reduction of vanadate ($V^{5+}$) ions to vanadyl ($V^{4+}$) ions and/or catalysis of such reduction. The inventor has also found that elevated vanadate ion levels in the body are associated with significant body weight gain rates. Whilst not restricting the scope of the present invention in any way it is believed by the inventor that the effectiveness of the method of the present invention is by means of the reversal and/or enhancement of reversal, of the Na-K ATPase inhibition in the body by vanadate ions.

The active compounds of the invention are usually administered in the form of a pharmaceutical formulation comprising a compound of the invention or bioprecursor thereof together with a pharmaceutically acceptable carrier therefor.

The carrier must be "acceptable" in the sense of being compatible with the other ingredients of the formulation and not deleterious to the patient. Such carriers may be solid, liquid or gaseous materials suitable for the purpose of administering the medicament by the desired route.

These pharmaceutical compositions may be administered orally or parenterally (including subcutaneous, intramuscular and intravenous injection) or as a suppository or pessary. In general the compositions are administered orally or parenterally. The words formulation and composition are used synonymously herein.

For parenteral administration the active compound may be presented in sterile solutions or suspensions in aqueous or oleaginous vehicles, which may also contain preservatives and material for rendering the solution or suspension isotonic with the blood of the patient. The formulations are conveniently presented in unit-dose or multi-dose sealed containers.

For oral administration the pharmaceutical compositions may be formulated as a draught in water or in a syrup, in capsules, cachets, boluses or tablets, as an aqueous or oleaginous solution or suspension or in suspension in a syrup, such suspensions optionally including suspending agents, or as an oil-in-water or water-in-oil emulsion. Flavouring, sweetening, preserving, thickening or emulsifying agents may also be included in the formulation.

Tablets may contain the active compound as a powder or granules optionally mixed with binders, lubricants, inert diluents or surface-active or dispersing agents and may be formed by compression or by moulding in inert liquid diluent. Such tablets may be scored and/or coated.

Capsules and cachets may contain the active compound alone or in admixture with one or more other ingredients. Capsules may also contain the active compound in aqueous or oleaginous solution suspension or emulsion optionally in association with other ingredients. For administration as a suppository or pessary the active compound may be presented in admixture with a suitable carrier such as cocoa butter and other material commonly used in the art, and are conveniently shaped by moulding. For administration in discrete unit dosage forms such as tablets, capsules, suppositories and pessaries as described above, the active compound is preferably present at from 1 mg to 400 mg, most preferably from 25 mg to 400 mg, per tablet, capsule, suppository or pessary in the case of methylene blue and from 25 mg to 1 g, most preferably 200 mg to 1 g for ascorbic acid and glutathione.

All the above formulations may be produced by standard processes comprising bringing the active compound into association with one or more pharmaceutically acceptable carriers.

The required effective dosage of the compound of the invention will of course depend on various factors such as the activity of the individual compound, the depth, and severity of the illness, and the responsiveness of the individual patient to the treatment regimen used. In general though the compound of the invention will be administered at a dosage in the range of from 0.1 mg to 2 g per kg body weight of the slimmer per day, preferably from 0.2 to 8 mg/kg in the case of methylene blue, from 5 mg to 2 g per kg bodyweight of the slimmer per day in the case of ascorbic acid and from 0.2 to 500 mg per kg bodyweight per day, preferably from 10 to 100 mg per kg bodyweight of glutathione. Advantageously the dosage is administered in two or more equal portions at approximately equal intervals.

Further preferred features of the invention will appear from the following examples.

Example 1

A double blind placebo controlled cross-over trial of ascorbic acid was carried out on 34 overweight subjects. Subjects were interviewed by a dietician who gave instructions on a 1200 calorie diet. The trial lasted 12 weeks. For the first 6 weeks half of the subjects received 3 grammes of ascorbic acid daily, and for the second 6 weeks they received similar placebo tablets. The other half of the subjects received placebo first and then ascorbic acid. 2 subjects did not complete the trial. All the subjects were weighed weekly.

| Results | |
|---|---|
| first 6 weeks: | |
| Subjects receiving ascorbic acid | lost a mean of 2.04 Kg |
| Subjects receiving placebo | lost a mean of 1.51 Kg |
| second 6 weeks: | |
| Subjects receiving ascorbic acid | lost a mean of 0.86 Kg |
| Subjects receiving placebo | lost a mean of 0.20 Kg |

In those subjects over 33% above ideal weight:

| first 6 weeks: | |
|---|---|
| Subjects receiving ascorbic acid | lost a mean of 2.89 Kg |
| Subjects receiving placebo | lost a mean of 0.67 Kg |
| second 6 weeks: | |
| Subjects receiving ascorbic acid | lost a mean of 0.72 Kg |
| Subjects receiving placebo | gained a mean of 0.13 Kg. |

Example 2

One subject who had been overweight for many years was treated for 8 weeks with methylene blue at a dosage rate of 300 mg/day. At the start of the procedure the subject was 42% above ideal weight but after eight weeks had lost 5.8 Kg without any regulation of diet. This latter result is particularly significant because of the great difficulty experienced by many persons in consistently adhering to strictly controlled diets over extended periods of time. On the contrary the method of the invention enables significant results to be obtained in a relatively short period of time with the method of the invention alone.

What is claimed is:

1. A method for bodyweight reduction of animals comprising administering to an animal in need of bodyweight reduction a bodyweight reducing effective dosage of 250 mg to 100 g per day of ascorbic acid or a physiologically acceptable salt and ester thereof.

2. A method as claimed in claim 1, wherein the compound is ascorbic acid.

3. A method for the treatment or prophylaxis of obesity in animals to reduce or control the bodyweight thereof comprising administering to an animal in need of said treatment or prophylaxis a therapeutically or prophylactically effective dosage of 250 mg to 100 g per day of ascorbic acid or a physiologically acceptable salt and ester thereof.

4. A method as claimed in claim 3, wherein the compound is ascorbic acid.

5. A method for bodyweight reduction of animals comprising administering to an animal in need of bodyweight reduction a vanadate ion induced Na-K ATPase inhibition reversing effective dosage of 250 mg to 100 g per day of a vanadate ion induced Na-K ATPase inhibition reversing agent which is ascorbic acid or a physiologically acceptable salt and ester thereof.

6. A method for the treatment or prophylaxis of obesity in animals to reduce or control the bodyweight thereof comprising administering to an animal in need of said treatment of prophylaxis a vanadate ion induced Na-K ATPase inhibition reversing effective dosage of 250 mg to 100 g per day of a vanadate ion induced Na-K ATPase inhibition reversing agent which is ascorbic acid or a physiologically acceptable salt and ester thereof.

* * * * *